United States Patent
Esteve et al.

(10) Patent No.: US 9,486,592 B2
(45) Date of Patent: Nov. 8, 2016

(54) MEDICINE DISPENSING DEVICE

(76) Inventors: Victor Esteve, Sao Paulo (BR); Eric Zembrod, Sao Paulo (BR)

(*) Notice: Subject to any disclaimer, the term of this patent is extended or adjusted under 35 U.S.C. 154(b) by 285 days.

(21) Appl. No.: 14/354,414

(22) PCT Filed: Oct. 27, 2011

(86) PCT No.: PCT/BR2011/000402
§ 371 (c)(1),
(2), (4) Date: Jul. 21, 2014

(87) PCT Pub. No.: WO2013/059889
PCT Pub. Date: May 2, 2013

(65) Prior Publication Data
US 2015/0080808 A1    Mar. 19, 2015

(51) Int. Cl.
| | |
|---|---|
| A61M 11/00 | (2006.01) |
| B65D 83/20 | (2006.01) |
| A61M 15/00 | (2006.01) |
| A61M 15/08 | (2006.01) |
| B05B 11/00 | (2006.01) |
| B65D 83/38 | (2006.01) |

(52) U.S. Cl.
CPC .......... *A61M 11/006* (2014.02); *A61M 15/009* (2013.01); *A61M 15/0025* (2014.02); *A61M 15/0026* (2014.02); *A61M 15/08* (2013.01); *B05B 11/3057* (2013.01); *B65D 83/206* (2013.01); *B05B 11/0037* (2013.01); *B65D 83/384* (2013.01)

(58) Field of Classification Search
CPC .......... A61M 11/006; A61M 11/007; A61M 11/08; A61M 11/00; A61M 11/04; A61M 15/0025; A61M 15/0026; A61M 15/009; A61M 15/08; B05B 11/3057; B65D 83/384
See application file for complete search history.

(56) References Cited

U.S. PATENT DOCUMENTS

| | | | |
|---|---|---|---|
| 3,272,391 A | | 9/1966 | Meshberg |
| 4,771,769 A | | 9/1988 | Hegemann et al. |
| 5,487,489 A | | 1/1996 | Weiss et al. |
| 5,915,597 A | * | 6/1999 | De Laforcade ...... B65D 83/205 222/182 |

(Continued)

FOREIGN PATENT DOCUMENTS

| | | |
|---|---|---|
| BR | PI9306950 | 1/1999 |
| BR | PI0416128 | 1/2007 |

(Continued)

OTHER PUBLICATIONS

International Search Report issued by the European Patent Office in the international application PCT/BR2011/000402 on Jul. 9, 2012.

*Primary Examiner* — Andrew Gilbert
(74) *Attorney, Agent, or Firm* — Henry M. Feiereisen LLC

(57) ABSTRACT

A medicine dispensing device includes a single injection molded part having a body and a cover pivotally interconnected by an articulation. The body has an annular base and a cylindrical encasement. The cover has a cylindrical portion and an upper dome-shaped portion. The cover is pivotal about the articulation so as to receive the body for axial alignment of the body and the cover. The dome-shaped portion is provided with cams which during the pivoting of the cover toward the body push down a springed actuator of a primary medicine packaging received in the body and fixed in the body by fastening and locking means, thereby causing release of the medicine in the primary medicine packaging.

9 Claims, 16 Drawing Sheets

(56) References Cited

U.S. PATENT DOCUMENTS

| | | | |
|---|---|---|---|
| 7,331,944 B2* | 2/2008 | Py | A61F 9/0008 222/162 |
| 7,708,732 B2* | 5/2010 | Norrie | A61M 5/31511 604/223 |
| 7,798,368 B2* | 9/2010 | Anderson | A61M 15/08 128/200.23 |
| 8,348,102 B2* | 1/2013 | Stradella | B65D 83/386 128/200.21 |
| 8,511,515 B2* | 8/2013 | Lemaner | A61M 15/009 222/162 |
| 8,881,944 B2* | 11/2014 | Paas | B65D 83/206 222/1 |
| 2002/0170928 A1* | 11/2002 | Grychowski | A61M 15/009 222/251 |
| 2004/0050869 A1 | 3/2004 | Jennings et al. | |
| 2005/0139615 A1 | 6/2005 | Stradella et al. | |
| 2006/0191959 A1* | 8/2006 | Davies | B05B 11/0032 222/162 |
| 2007/0051754 A1* | 3/2007 | Strand | B65D 83/206 222/402.13 |
| 2007/0095853 A1* | 5/2007 | Bonney | B05B 11/3056 222/21 |
| 2007/0131717 A1 | 6/2007 | Davies et al. | |
| 2007/0138207 A1* | 6/2007 | Bonney | A61M 11/08 222/162 |
| 2007/0164049 A1* | 7/2007 | Bonney | B05B 11/3056 222/162 |
| 2008/0116223 A1* | 5/2008 | Stradella | B65D 83/386 222/162 |
| 2008/0237264 A1* | 10/2008 | Auerbach | B05B 11/3056 222/162 |
| 2008/0272144 A1 | 11/2008 | Bonney et al. | |
| 2010/0308082 A1* | 12/2010 | Lamble | A61M 15/009 222/162 |
| 2011/0006083 A1* | 1/2011 | Walters | B65D 83/206 222/153.11 |
| 2013/0144215 A1* | 6/2013 | Esteve | B05B 11/30 604/151 |

FOREIGN PATENT DOCUMENTS

| | | |
|---|---|---|
| BR | PI0507383 | 7/2007 |
| BR | PI1000731 | 10/2011 |
| DE | 196 10 456 | 9/1997 |
| FR | 2 812 826 | 2/2002 |
| FR | 2 859 464 | 3/2005 |
| FR | 2 882 349 | 8/2006 |
| FR | 2 889 691 | 2/2007 |
| FR | 2 889 692 | 2/2007 |
| JP | 10-179739 | 7/1998 |
| WO | WO02/49698 | 6/2002 |
| WO | WO03/061843 | 7/2003 |
| WO | WO2005/044354 | 5/2005 |
| WO | WO2005/075103 | 8/2005 |
| WO | WO2009/068877 | 6/2009 |

* cited by examiner

MEDICINE DISPENSING DEVICE

CROSS-REFERENCES TO RELATED APPLICATIONS

This application is the U.S. National Stage of International Application No. PCT/BR2011/000402, filed Oct. 27, 2011, which designated the United States and has been published as International Publication No. WO 2013/059889 A1.

BACKGROUND OF THE INVENTION

FIELD OF THE INVENTION

The present invention refers to a manual drive mechanism ordinarily in the form of outer-packaging, designed to internally receive a primary packaging traditionally used to contain a medicine of any kind in liquid state or having easy fluidity. This medicine is generally of the kind to be applied in spray form or drops, such as occurs in ophthalmic or nasal treatments. In this condition, the aforementioned primary packaging also has an upper part in the form of an actuator nozzle internally valved to release doses in spray, drop or jet form. This actuator nozzle is integrated with an internal valve system and metered dose pump which is driven by pressing said nozzle which, accordingly, has a flange for this purpose.

Hence, the present invention provides a body which, besides being an anatomical grip, includes in this same grip a trigger precisely to press the mechanism of the actuator nozzle and, consequently, drive said pump to release the output of the medicine in spray form.

Flask or medicine primary packaging is understood to be any recipient having a dispensing nozzle with an actuator inside with a dosing pump and valve to dispense the medicine in the form of jets, whether spray or otherwise, and also in drop dose form.

STATE OF THE ART

Currently there are different devices used for the same purpose, each having its constructive particularities, such as those taught in documents: BRPI9306950, BRPI0416128, BRPI0507383, BRPI1000731 (PCT/BR2011/000066), DE19610456, FR2812826, FR2859464, FR2882349, FR2889691, FR2889692, JP10179739, U.S. Pat. Nos. 3,272,391, 4,771,769, 5,487,489, 2002170928, WO0249698, WO03061843A1, WO2005044354 and WO2005075103, WO2009068877.

There is no doubt that the above devices and others present suitable means to dispense the medicine, whether in spray form or otherwise, however, in most cases, said mechanisms have a considerable number of articulated components and levers which, despite working satisfactorily, add details to complicate the manufacture, assembly and the working of the combination, consequently, considerably increasing its end cost as well.

Moreover, some of these devices, such as: DE19610456, FR2812826, DE19610456, WO2005075103 and WO2009068877, present as predominating characteristic a drive by levers that acts or depends directly on contact with a component of the pump as in its base, or adjacent parts as in its actuator and, also, in some cases, the mechanism requires the medicine flask itself to have some detail to be coupled to the drive mechanism. Obviously all this ultimately interferes in the industrial viability of the combination, to define a complex combination not only to produce, but also to assemble, consequently, the end cost also proportionally increases in relation to said advantages.

Another factor also not found in the devices known in the art is the fact that they do not have resources or flexibility to adjust the drive strength and speed, which are significant for determining the spray pattern.

Therefore, the known devices present a considerable number of components, which requires longer assembly time. The same is true for the production of the components and, ultimately, besides characterizing a substantially complex mechanism, also present manufacturing costs which reflects the industrial complexity of the combination.

To solve the problems above, the applicant initially created patent BRPI1000731, also entitled "MEDICINE DISPENSING MECHANISM" wherein there are provided just two components responsible for driving the medicine flask pump. The first component is a trigger combined with a cup-shaped base which is the second component, wherein the latter is the support cradle for fastening the bottom or lower end of the medicine flask. Said trigger has an ordinarily semicircular part which, from the outside, configures an anatomical finger support area for driving in the manner of a press button, whereas from the inside said trigger, besides involving the medicine flask, also presents an elongated lower part in the form of two slanted arms, one on each side of the flask, whose lower ends each have an ordinarily horizontal protraction, where one of its ends is articulately integrated with the corresponding arm, and the median portion of said protraction has a cavity on the lower side of its articulated support on the corresponding inner side of the body, where said protraction moves like a seesaw (lever) and, further, its upper face describes a "cam surface" which supports radial projections existing on the edges of said cup, such that the latter can be displaced upwards or downwards, that is, when pressing the trigger the lower ends of its arms act on the corresponding ends of the seesaw protractions and, with this, its cam surface makes said cup be displaced upwards and downwards according to a sufficient extent to drive the pump of the medicine flask and dispense its content in the form of spray.

Therefore, BRPI1000731 has the advantage of embodying a mechanism defined by just two mobile components, the trigger and the cup, where the first is a single injected component which combines parts specially designed and strategically positioned such that each part can have one function and, thus, a single component alone is capable of carrying out a succession of movements which ultimately displace said medicine flask upwards and, at this point, its pump mechanism is driven to dispense the medicine contained inside in a spray form. The succession of movements is the main characteristic of the mechanism of BRPI1000731, since, the part that acts as trigger is anatomically positioned and, accordingly, when pressed inwards, makes the angular arms be equally displaced, making its ends be displaced downwards and, at this moment the second movement occurs, being the actuation of the "cam system", that is, the protraction in seesaw form has its corresponding end displaced downwards, causing a seesaw (lever) effect and, with this, a third movement occurs on the "cam surface", making the cup be displaced upwards, causing the drive of the pump mechanism of the medicine flask.

An advantageous aspect of BRPI1000731 is, without a doubt, its drive button, because with a single component, it is possible to execute various movements to drive the medicine flask pump/valve mechanism, which is not the case in the devices of the prior documents, where said movements are obtained with a greater number of components.

Another advantageous aspect of BRPI1000731 relates to the arrangement of its upper portion, conceived to partially cover the nozzle of the dosing pump actuator, making its ergonomics safer to be introduced into the nostrils, even for pediatric use.

Another advantage provided by BRPI1000731, although optional, is that it provides means to exchange the empty medicine flask for a refill unit, which is carried out easily and quickly by using fast internal engagement and disengagement means on the flange of the medicine flask, and these means are driven by lightly pressing the corresponding sides of the body of the actuator.

Although BRPI1000731 was developed with a reduced number of parts, it still required assembly of the combination, and also required strict quality control, principally for the part defined as the trigger.

Therefore, in this kind of device it was still desirable to develop a single-part version in order to eliminate entirely the assembly step and, furthermore, to simplify the injection mold, consequently also reducing the end cost of the combination.

It is also desirable to develop a device capable of receiving primary packaging with different capacities, varying just the height of its flask and keeping the closure and pump characteristics.

In contrast to known versions, it is desirable that the device have a quick-fit primary packaging system, said quick-fit system being equipped with automatic locking, without complications both for the distributor of the medicine and also for the end user.

SUMMARY OF THE INVENTION

In light of the above circumstances, the present invention proposes a totally renovated device, single-part injected, thus having two main parts, one defined as body while the other is defined as pressing cover, both articulatedly interconnected, consequently form a single part which, in the injection process, are shaped open, and also said body has a lower section ordinarily in the form of circular base, the inner diameter of which is defined by a kind of flange or locking collar comprised of a collar having substantially flexible tabs, such that said diameter can increase and decrease at the point in which the primary packaging is fitted, that is, said flange passes through its pump and through its lid and, in the latter, the through-passing of said lid occurs with interference, such that the tabs or flange can sufficiently arch for the passage of the lid and, after this occurs, the tabs or flange returns to its lower primitive diameter and fits between the interstice formed between the body and the lower edge of said lid, consequently, locking occurs between the device and the primary packaging.

Above said circular base is a partial, vertical half-round encasement, enclosing practically half the packaging, and also on its top there is articulatedly interconnected the part defined as pressing cover which, in turn, besides encasing the other half of the primary packaging, acts as an L-shaped lever, that is, it firstly has an upper opening to expose the nozzle of the packaging, while internally it has a pair of projections that configure a kind of cam which, in turn, is positioned supportedly on the mobile drive part of the springed pump of the primary packaging. In this condition, cam and cover form an L-shaped lever defined as pressing cover. Therefore, it is noted that the body and the cover involve practically all the primary packaging and, also, anatomically combine to form a device in the form of pressable (squeezed and unsqueezed) grip and, with this, there occurs the angular movement of the pressing cover and, with it, said cam is displaced to two distinct positions, one of them makes the pump move downwards and the other makes said pump return to its original position, consequently, said drive sequence can be repeated intermittently, causing the output of the medicine in spray or drop form.

The present invention achieves the first objective which is the configuration of a single-part drive device, eliminating the assembly step and, also, simplifies the injection mold, consequently considerably reduces the end cost of the combination.

Another objective achieved by the device in question is the fact that it is capable of receiving primary packaging with different capacities, the only variation being the height of its flask (recipient), the closure and pump characteristics being maintained.

Another objective achieved by the device in question is the fact that it has a primary packaging quick-fit system, said quick-fit system being equipped with automatic locking, without complications both for the distributor of the medicine and also for the end user.

Another objective is to cover part of the actuator nozzle of the primary packaging valve, reducing its exposure, making it anatomical to increase the security in the application in ophthalmic or even nasal use.

Another objective achieved by the device in question is the fact that it presents resources to be re-used, that is, that allow the use of a refill.

DESCRIPTION OF THE DRAWINGS

For an improved understanding, there follows a detailed description of the present invention, with references to the accompanying drawings.

DETAILED DESCRIPTION OF THE INVENTION

Figure 1:
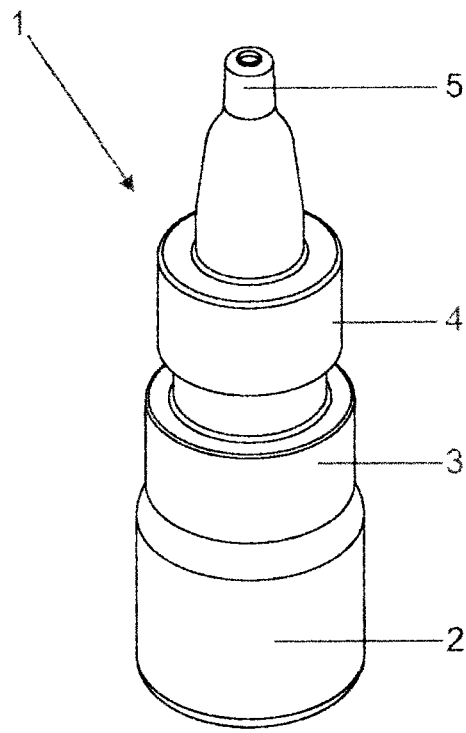
FIGS. 1 to 3 represent, respectively, two perspectives and a side view, highlighting the details of a primary packaging of medicines with flask recipient and dosing pump/valve.
Figure 2:
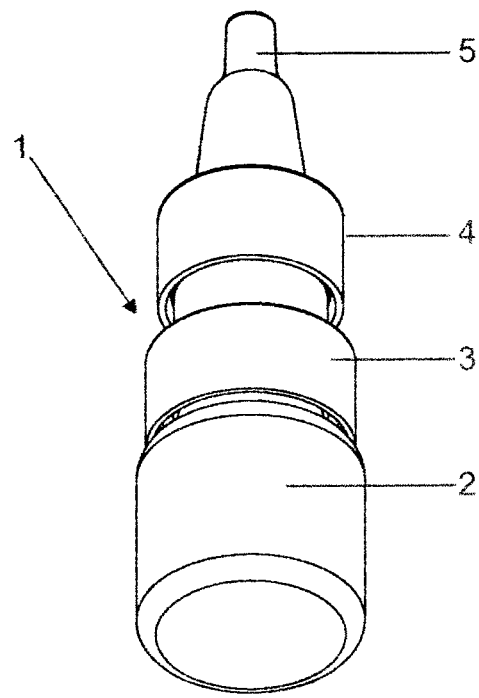
Figure 3:
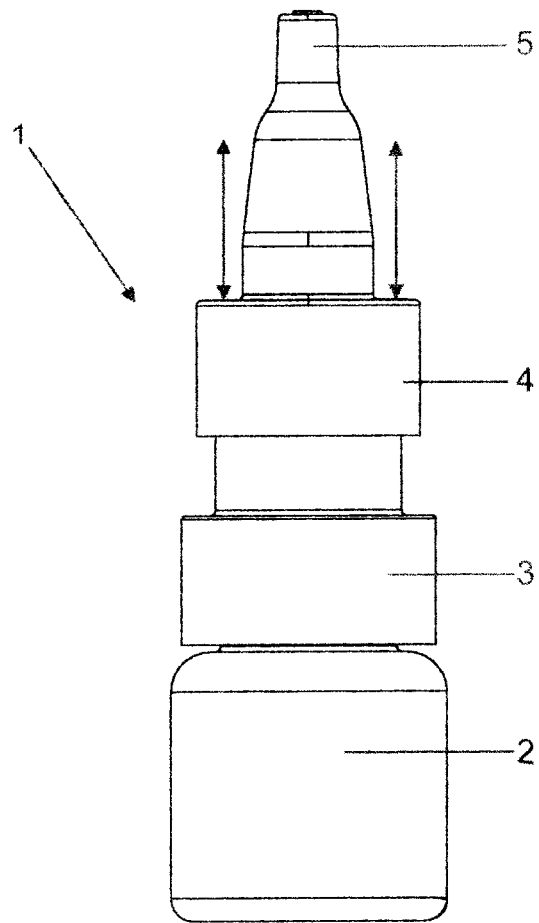
Figure 4:
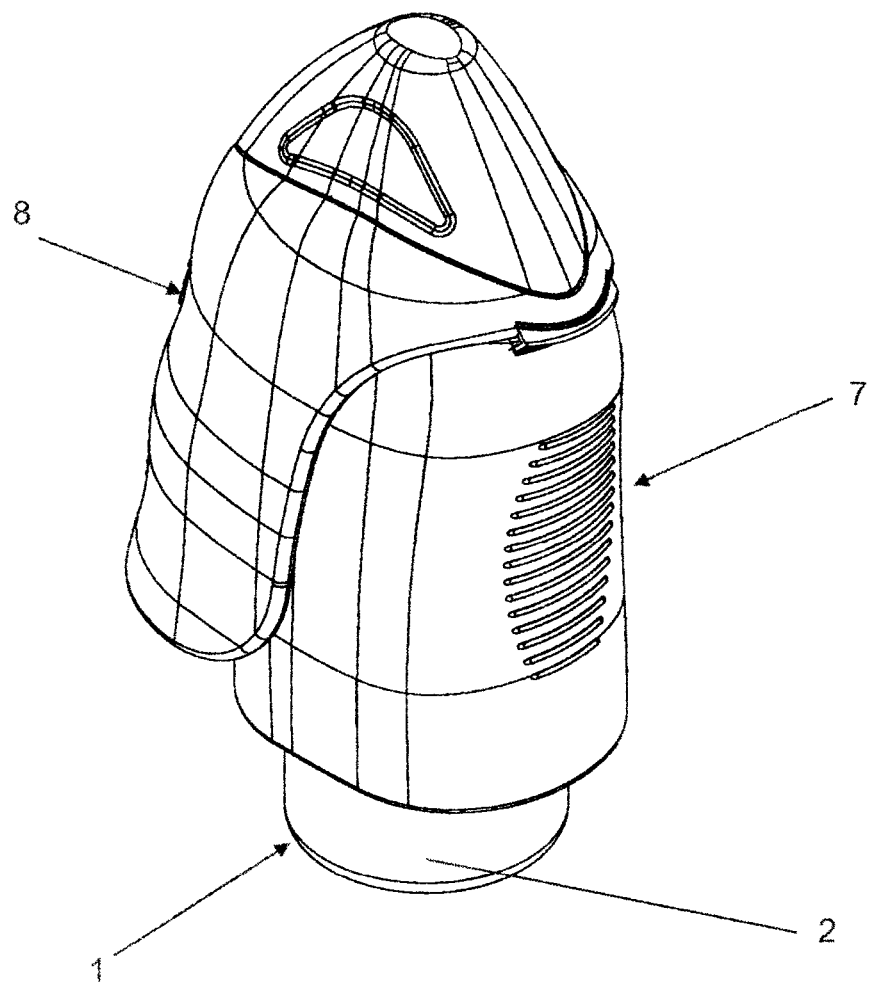
FIGS. 4 and 5 show two perspectives of the device in question fully assembled with a medicine primary packaging.
Figure 5:
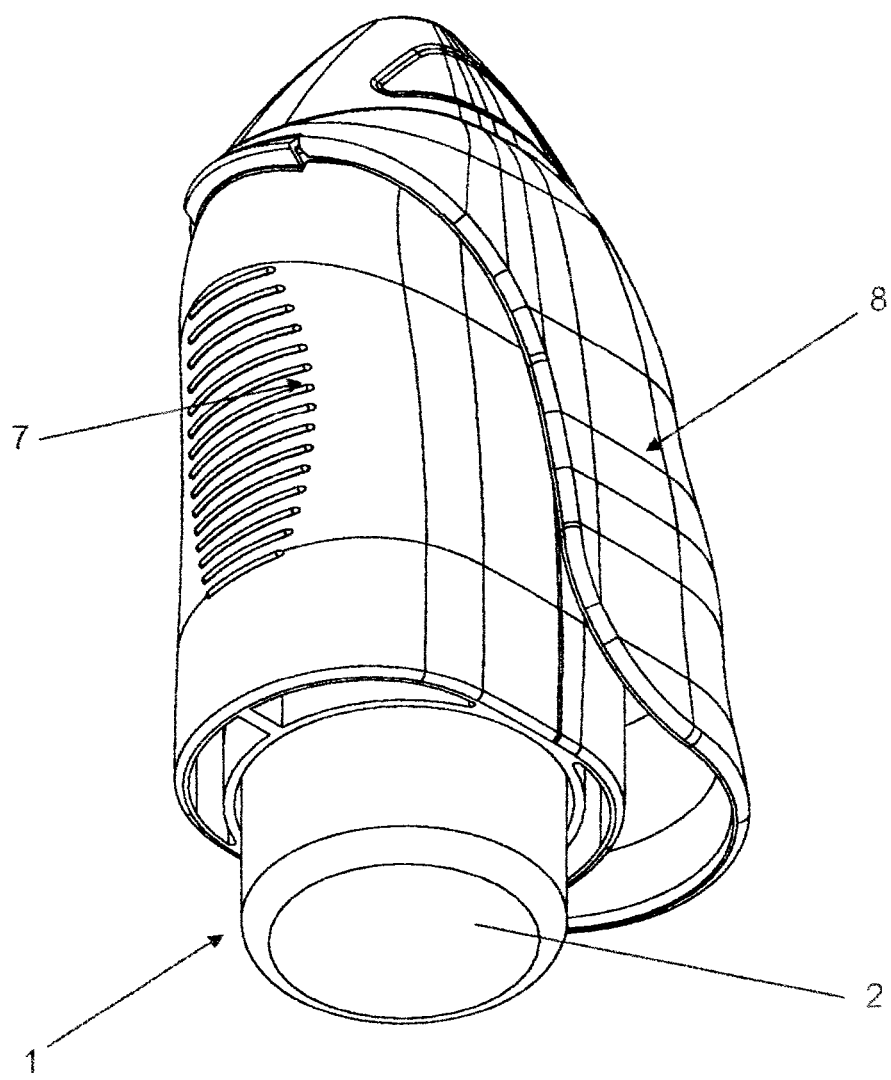
Figure 6:
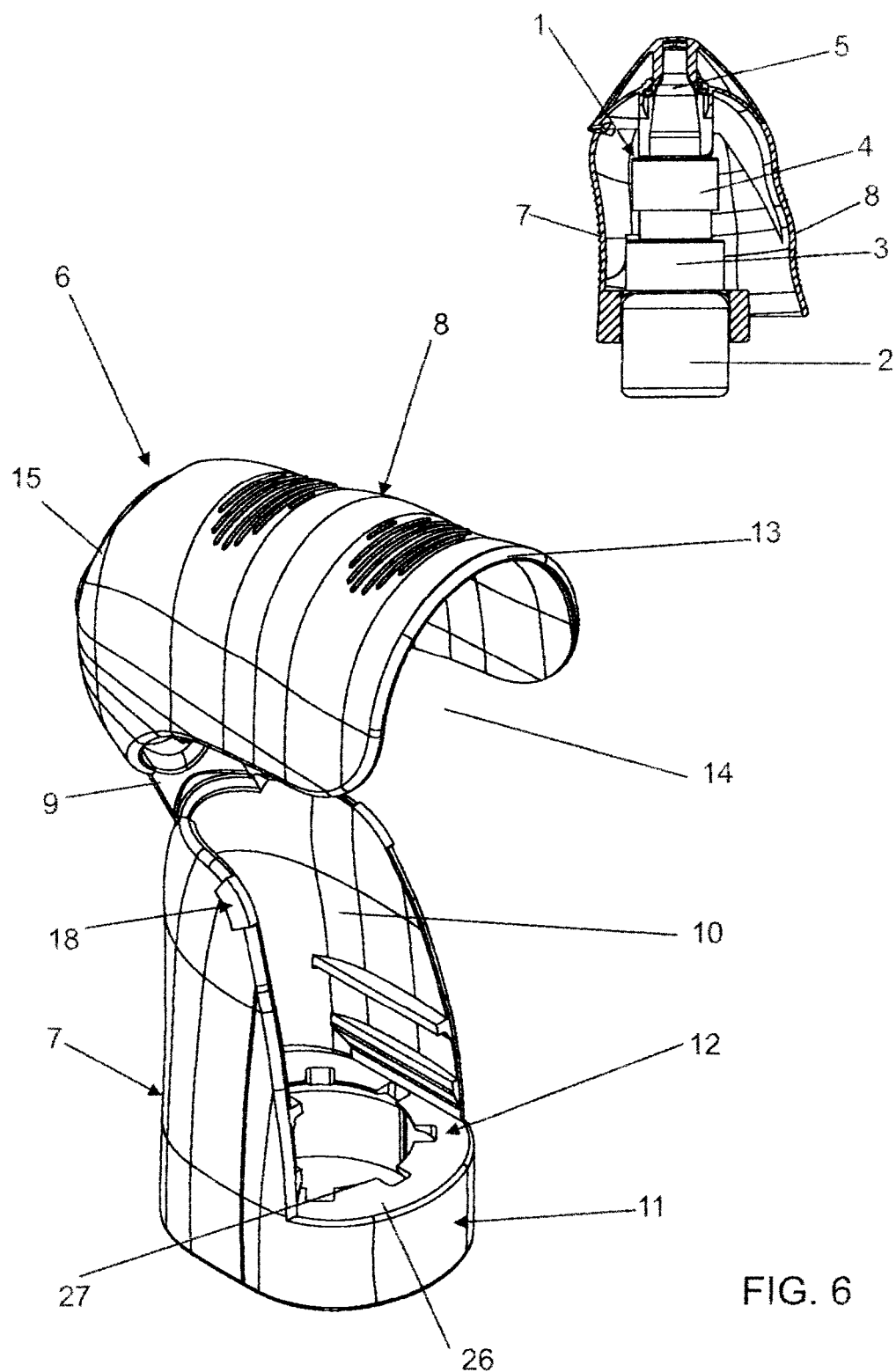
FIGS. 6 to 9 illustrate perspectives from different angles, showing details of the device in question when leaving the mold (open)
Figure 7:
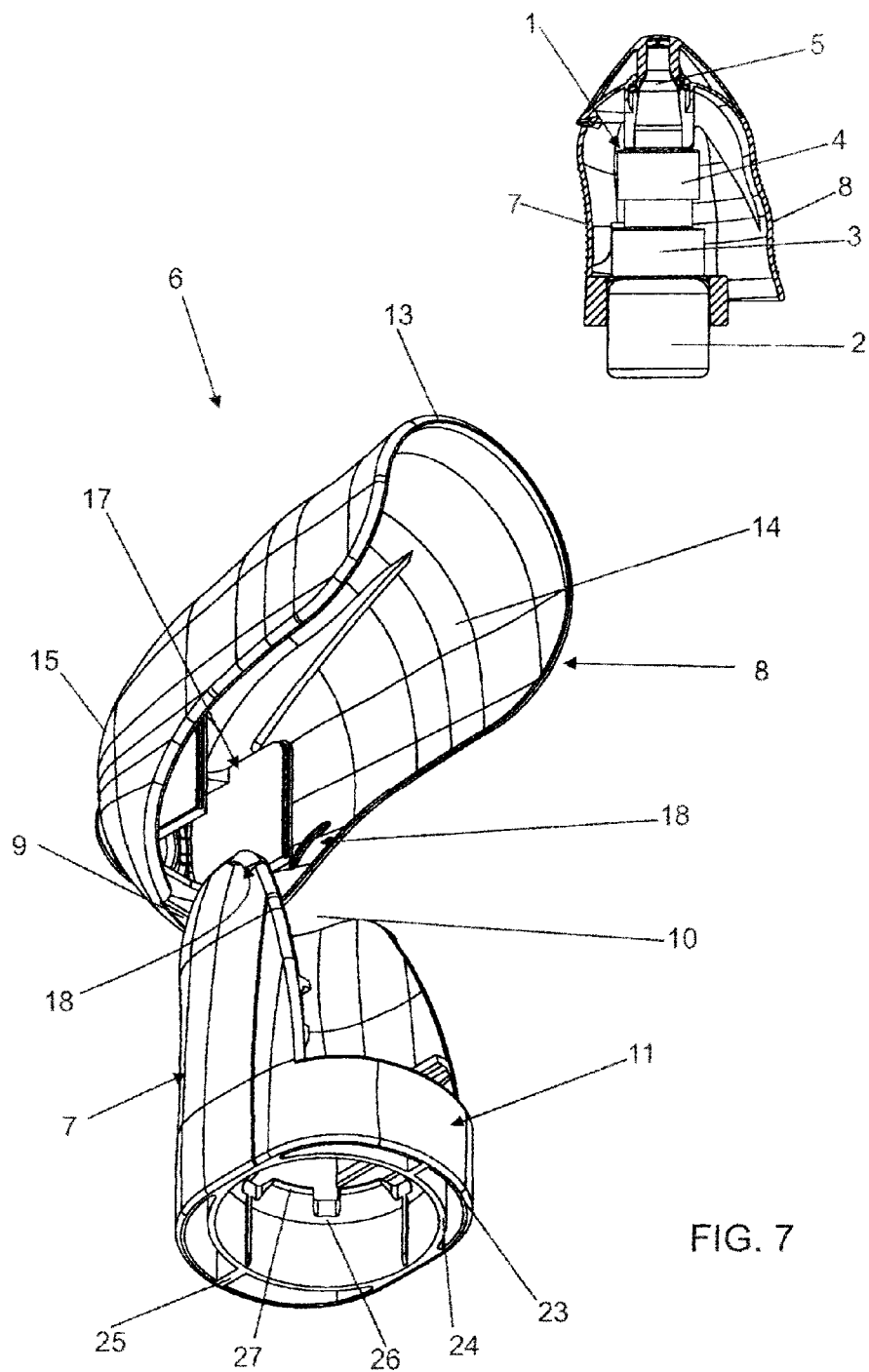

According to these illustrations and the details therein, the present MEDICINE DISPENSING DEVICE, as illustrated in FIGS. 1 to 3, is of the kind to be used with a traditional medicine packaging (1), comprising a cylindrical flask (2) and related lid (3) which, in turn acts as an assembly base for a springed actuator (4) and respective dispensing nozzle (5), inside said actuator there being a combination that configures a dosing pump/valve (not illustrated) for the medicine contained in the flask (2).

As indicated by the arrows in FIG. 3, the springed actuator (4) is alternately upwardly and downwardly displaceable, making the pump/valve start dispensing the medicine through the actuator nozzle (5).

The medicine may be dispensed in the form of spray, drops, jets, or another suitable dosed form, since, said combination hereinafter identified as primary packaging (1) may always contain a considerable variety of medicines, such as those in liquid state or having easy fluidity, notably used for treating the eyes, ears, nose and throat.

Still referring to FIG. 3, the medicine packaging (1), by itself, is already a substantially efficient dispenser, since, pressing its spring actuator (4) drives the pump/valve and, with this, an exact dose is dispensed by the dispensing nozzle (5) previously positioned at the site to be treated.

Although the primary packaging (1) incorporates a drive so that it can normally be normally driven by its springed actuator (4), in many cases, a more anatomical form of drive is desirable, not only to facilitate the application of the medicine, but also to make the drive position more comfortable, including the drive by using only the flask may present a certain complexity for users such as children, the elderly or those who, for some reason, have poor motor skills.

To solve these and other drawbacks and make the application safer, various drive devices have been created, such as all those listed previously, including that of the present invention, are designed to contain inside the medicine packaging (1) and, with the latter, combine means so that its springed actuator (4) can be driven (pressed and released) with greater ease, comfort and less effort, making it recommended for adults and children.

Figure 8:
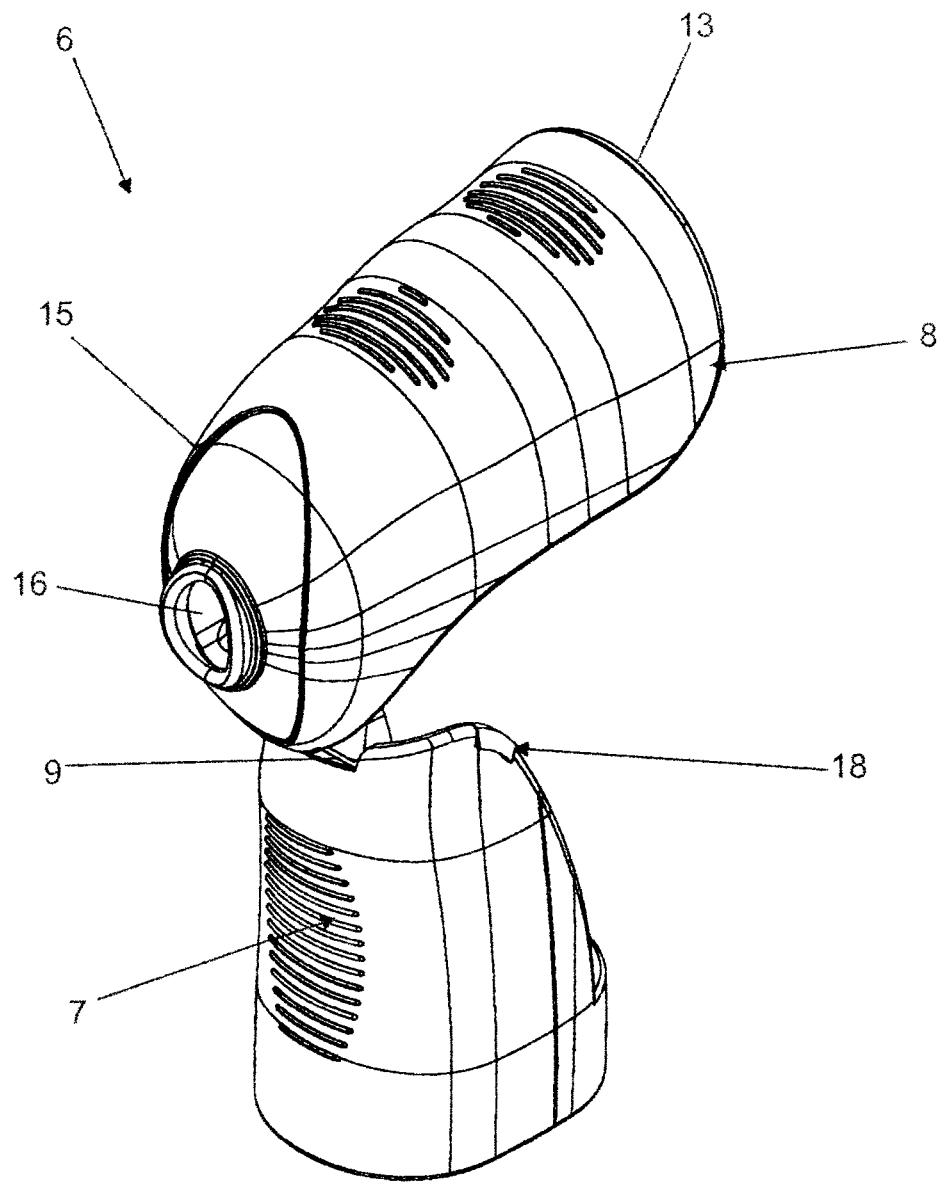
Figure 9:
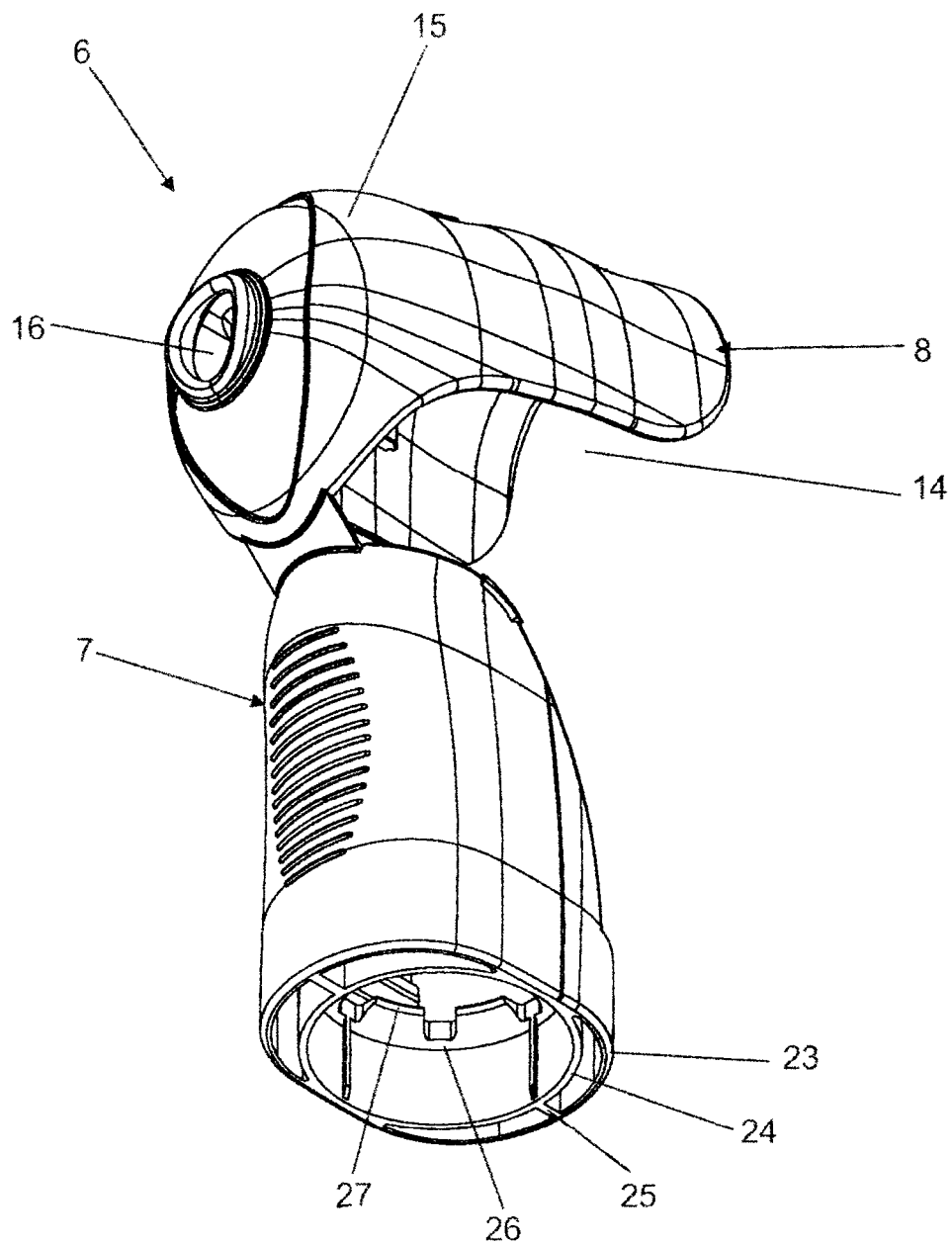
Figure 10:
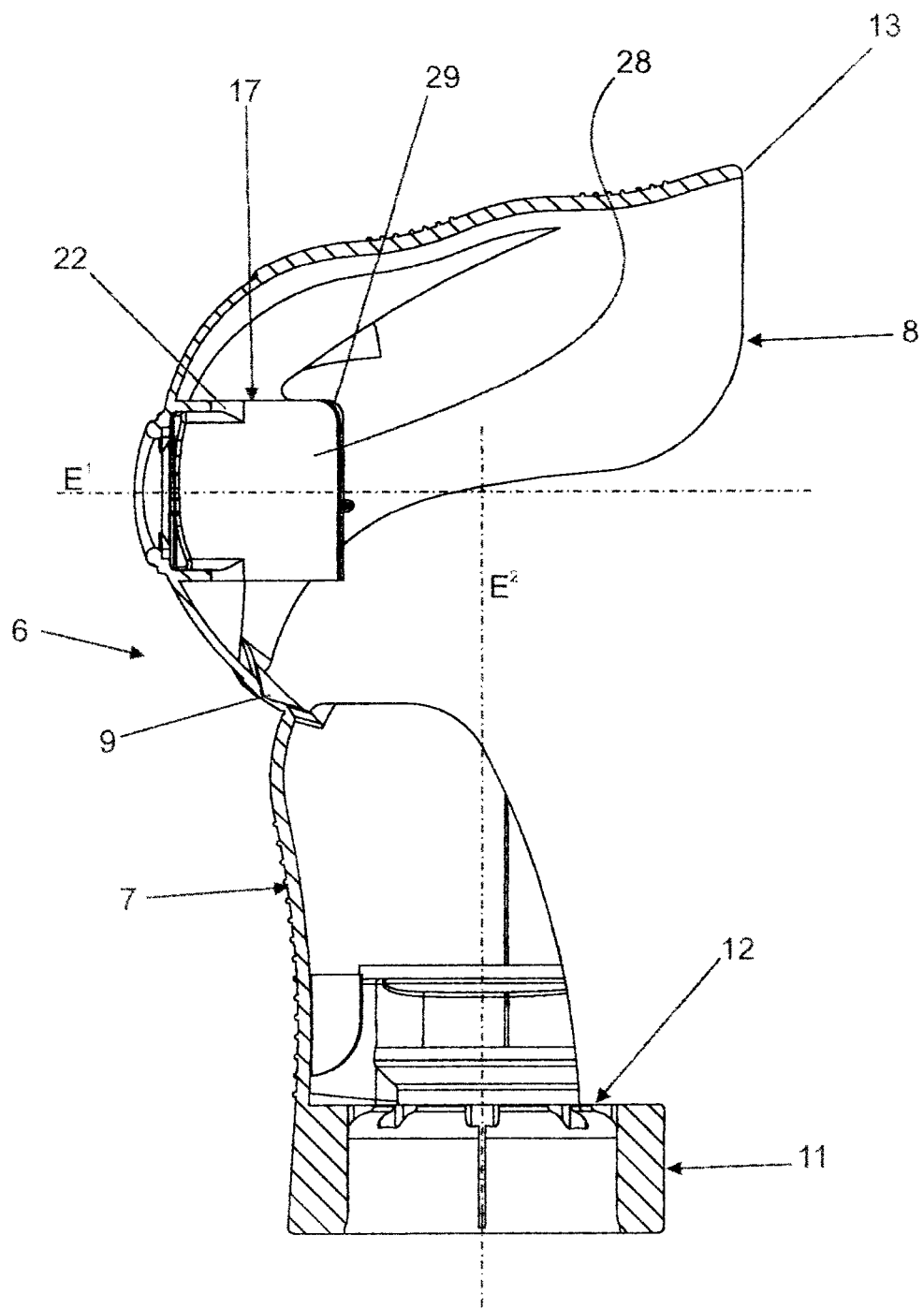
FIG. 10 is a cross-sectional side view of the device open.

As illustrated in FIGS. 4 to 7, the present mechanism is provided to encase and be fitted downwardly over the medicine primary packaging (1), partially exposing the lower part of the flask (2), and also uses the flatness of its bottom to standing support of the combination, as also shown in FIG. 8.

Figure 11:
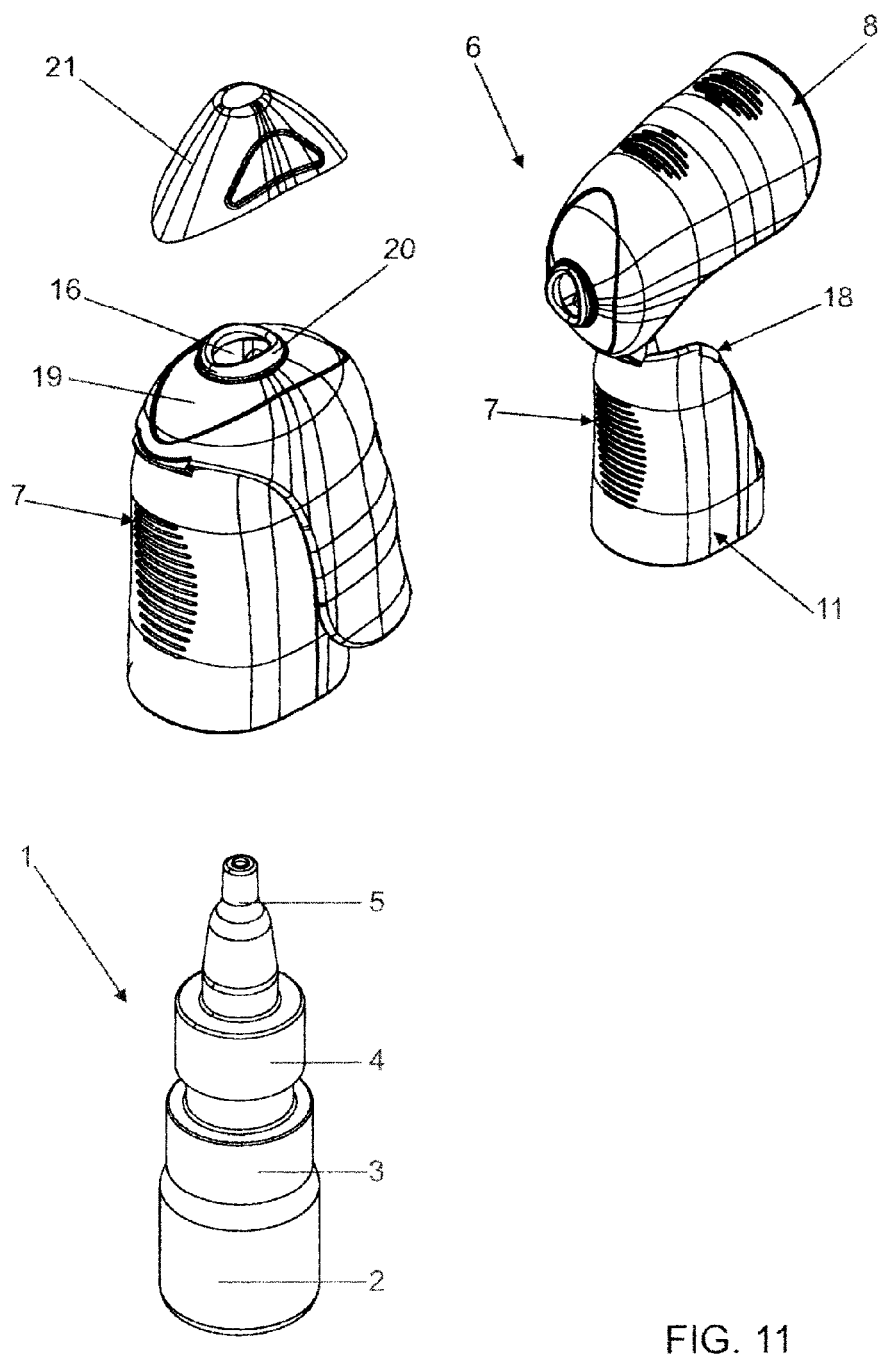
FIGS. 11 and 12 are exploded isometric views, showing the combination from different angles.
Figure 12:
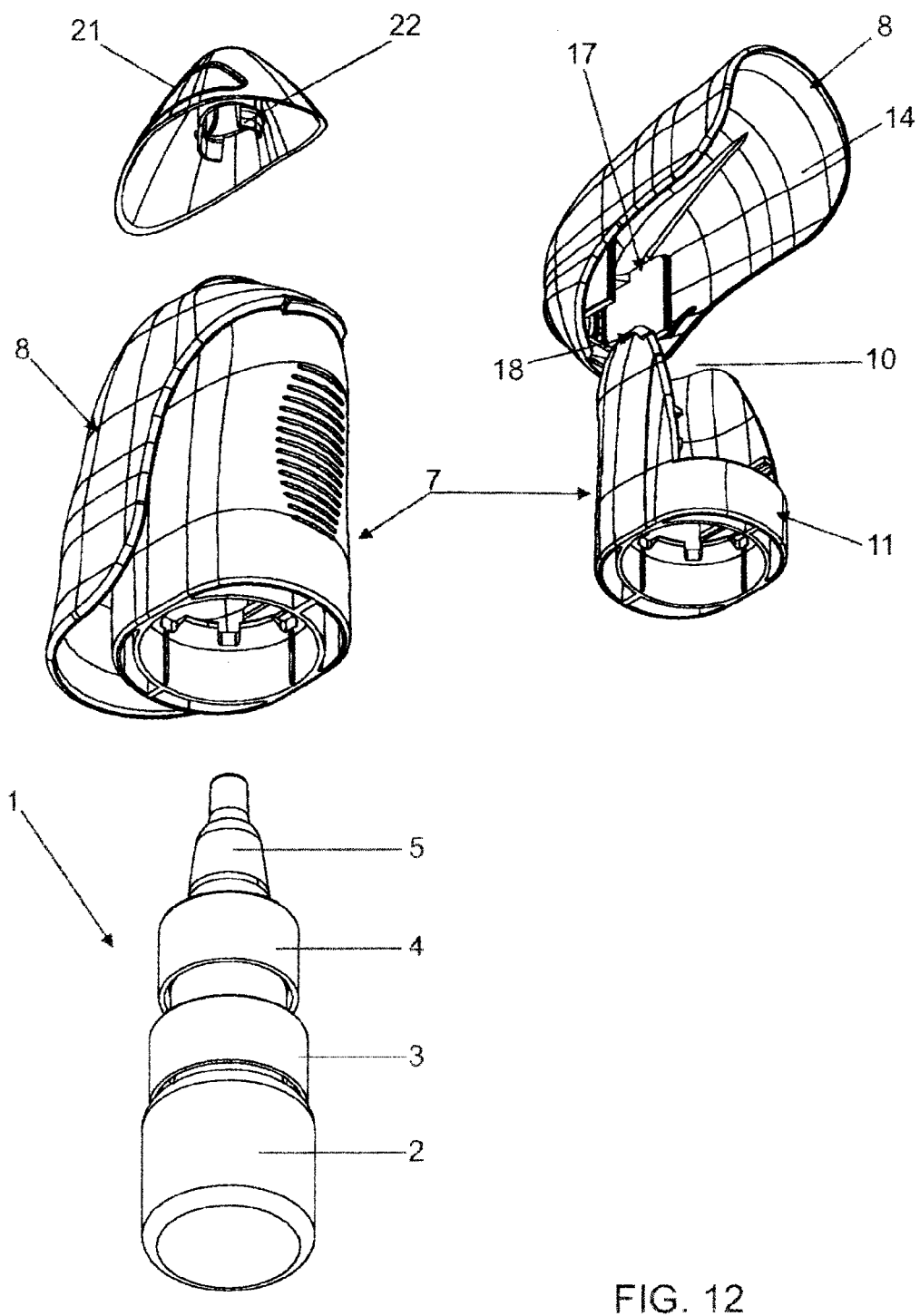
Figure 13:
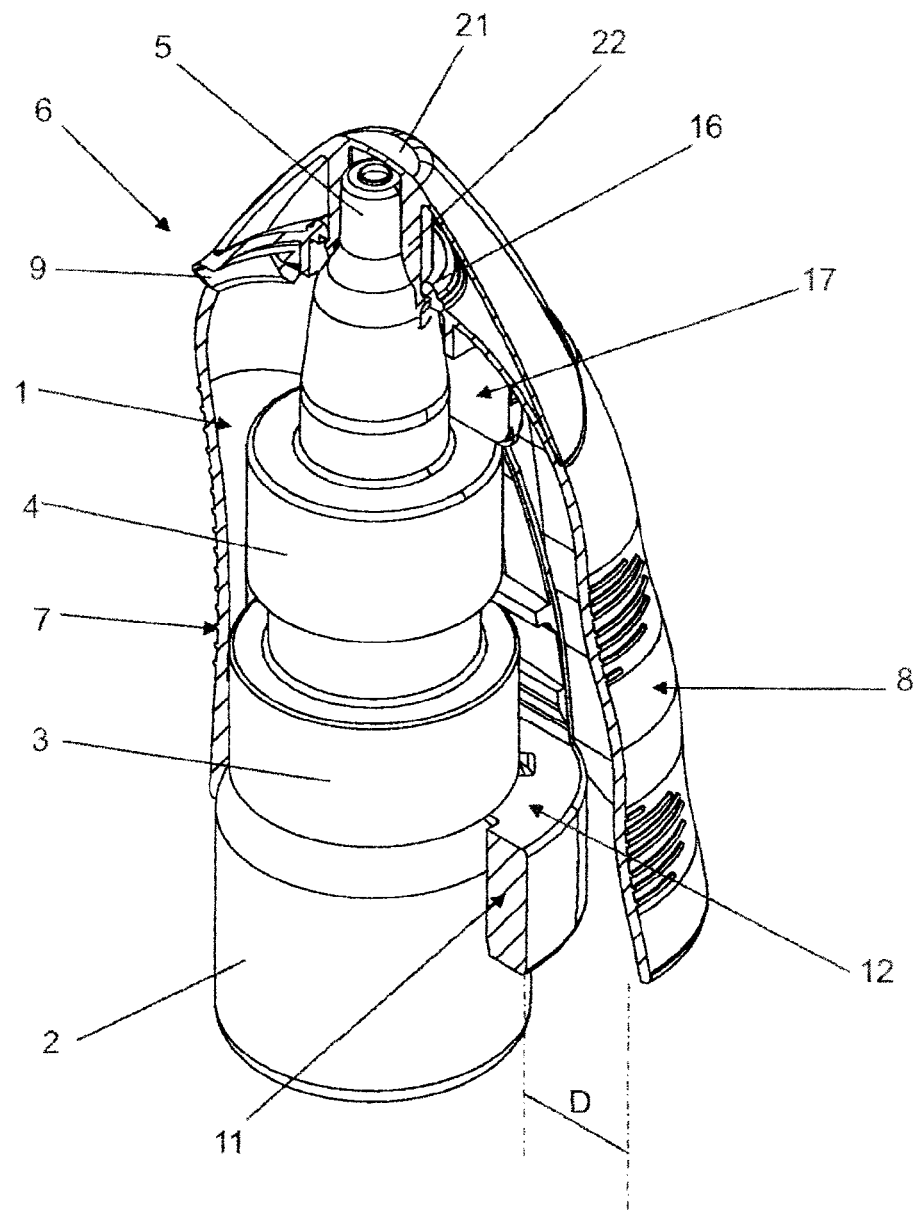
FIG. 13 illustrates a perspective of the assembled combination with a medicine primary packaging and, in this case, the device is depicted in cut-off view.

As illustrated in FIGS. 6 to 10, the present MEDICINE DISPENSING DEVICE is characterized by comprising:

a single injected part made of plastic material (6);
said single part is defined by two main ordinarily semi-cylindrical parts, a lower one that constitutes the body (7) and an upper one that constitutes the pressing cover (8), both with the tops articulatedly interconnected (9);
the body (7) is defined by an ordinarily vertical, semi-circular encasement, whose open side (10) faces forwards, and also on its upper edge there is integrated the articulation (9) of the pressing cover (8), while the lower edge is integrated to the outer diameter of a base (11), ordinarily annular, whose inner diameter has means (12) for fastening and locking the primary packaging (1), more precisely between its body (2) and its lid (3), maintaining its dispensing nozzle (5) above the articulation (9);
the main lid (8) is defined by an ordinarily semi-circular part (13), whose open side (14) faces rearwards and has sufficient width and depth to encase the entire region of the open side (10) of the body (7), but also its upper part funnels to form a dome (15) with a circular through-opening (16) of the dispensing nozzle (5) of the primary packaging (1);
the pressing cover (8) has a double cam (17) positioned below the circular opening (6) and arranged to be supported on the springed actuator (4) and press it downwards when said pressing cover (8) is pressed;
the single part (FIG. 10) made of plastic material (6) is injected in the open position, such that the body (7) and the pressing cover (8) have their longitudinal ($E^1$) and ($E^2$) orthogonally disposed;
the single part made of plastic material (6), as illustrated in FIGS. 11, 12 and 13, is moved to the closed position when it is used, displacing the pressing cover (8) downwards until it is axially aligned with the body (7) and, in this position, the open portions (10) and (14) of the two parts combine and the side edges of the pressing cover (8) slidably overlap the corresponding edges of the body (7) and, thus, the two parts combine to form a grip with anti-slip surfaces and, also, said pressing cover (8) is kept in the position of use by side retention means (18), however, said retention is limited (FIGS. 13 and 14) keeping the lower edge of said pressing cover (8) away from the annular base (11) in accordance with a sufficient distance (D) such that said cover (8) is displaced (pressed) until it meets said annular base (11), moving the cam (17) to the second drive position (FIG. 17) of the springed actuator (4) of the medicine packaging (1); and
the pressing cover (8) presents its dome (15) with a garret (19) and the opening (16) has a fastening collar (20), both combine to receive a lid (21) which, besides covering the exposed part of the dispensing nozzle (5), internally has a fast-engagement clip with the collar (20).

Figure 14:
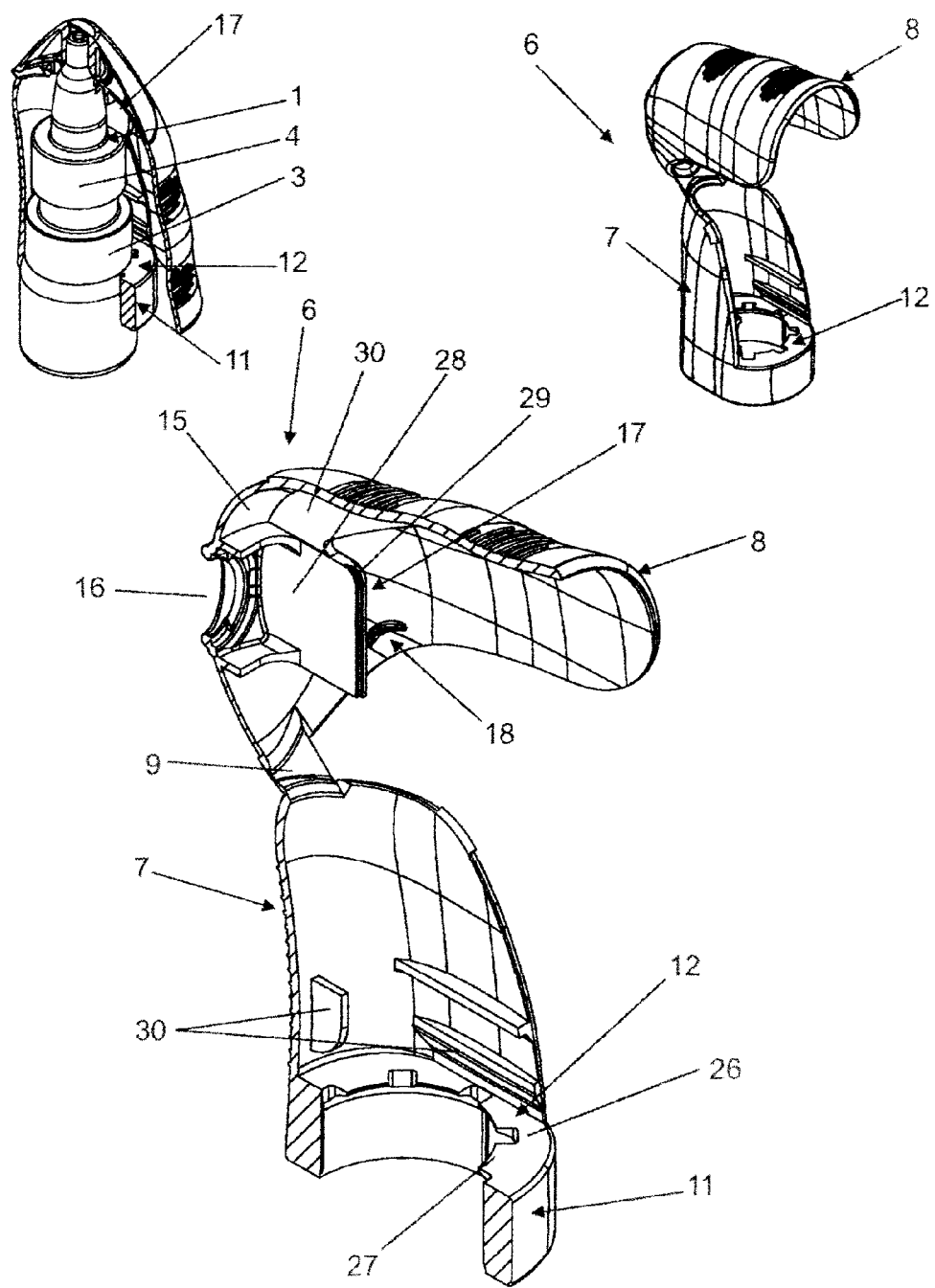
FIGS. 14 and 15 are isometric cut-off views showing the device open.
Figure 15:
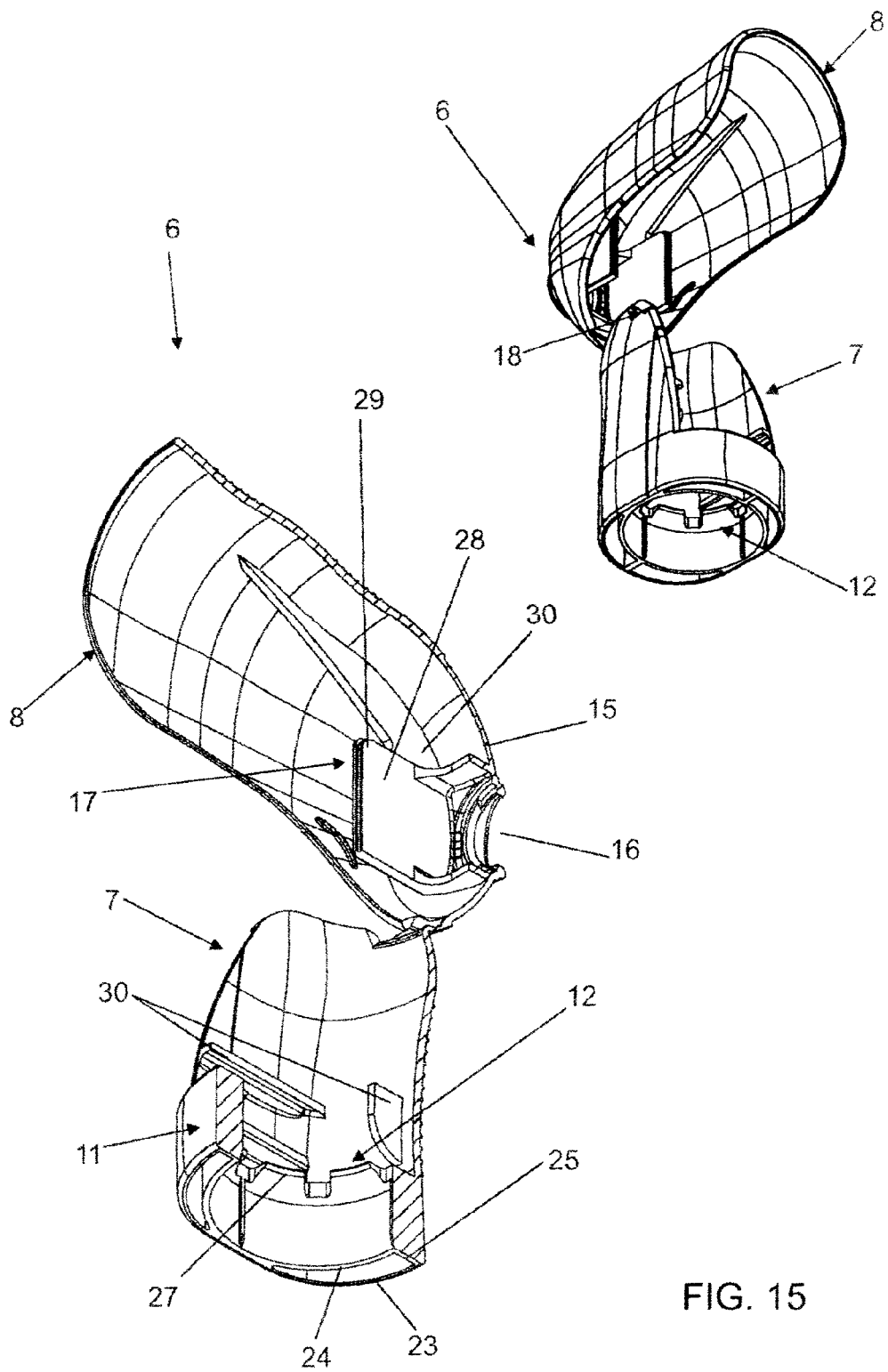

As illustrated in FIGS. 14 and 15, in a preferred construction, the base (11) is formed by two concentric walls, an ordinarily ovoid external one (23) and a circular one (24), interconnected by radial walls (25) and by an upper closure wall (26) which, in turn, is integrated to the fastening and locking means (12) of the primary packaging (1).

In a preferred construction, the fastening and locking means (12) of the primary packaging (1) are defined by the inward protraction of said closure (26) transforming it into an inner flange which, in turn, has a plurality of equidistant notches, forming an ordinarily dented part or with a plurality of coplanar, trapdezoidal tabs (27), all equally flexible and define an internal diameter slightly greater than the external diameter of the lid (3) of the packaging (1) and sufficient to be flexed when passing through said lid and returning to the original position when they surpass its lower edge, where said tabs promote a suitable locking of the packaging (1).

Still referring to FIGS. 14 and 15, in a preferred construction, the double cam (17) is formed by two vertical walls (28), which emerge from the inner face of the dome (15), but also between the same there is positioned the circular opening (16) and, also, the lower edges of said walls (28) are horizontally aligned and positioned in parallel on the springed actuator (4) of the packaging (1), and, further, the corners (29) of the same side of said walls preferably have a sufficient angle to form rounded support pressing points against the springed actuator (4) of the packaging (1).

The side retention means (18) are preferably teeth in the form of opposite wedges disposed next to the edges that encounter the body (7) and the pressing cover (8).

The inner faces of the body (7) and the pressing cover (8) have different projections (30) which, besides being structural, end in geometries that adjust against the profile of the packaging (1) to stabilize it in the position of use.

In some cases the medicine primary packaging (1) has a lid (not illustrated) fitted in its dispensing nozzle (5) and, thus, it may sometimes be desirable to maintain said lid, consequently, the lid (21) of the device may be eliminated, along with its fastening and locking details, however, in this case, the opening (16) presents sufficient diameter for exposing the dispensing nozzle (5) and its respective lid.

Figure 16:
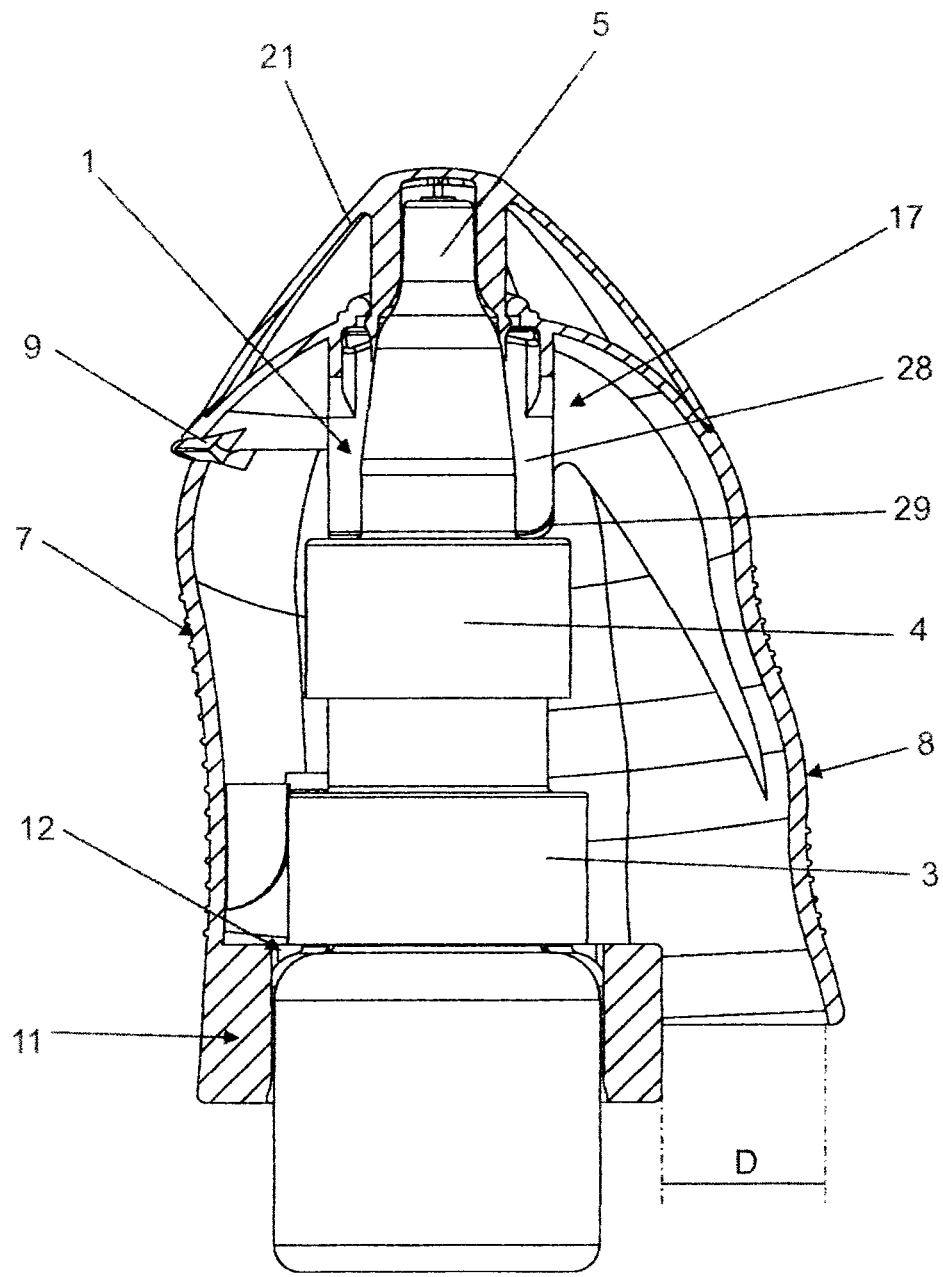
FIGS. 16 and 17 reproduce side cut-off views showing the workings of the device.
Figure 17:
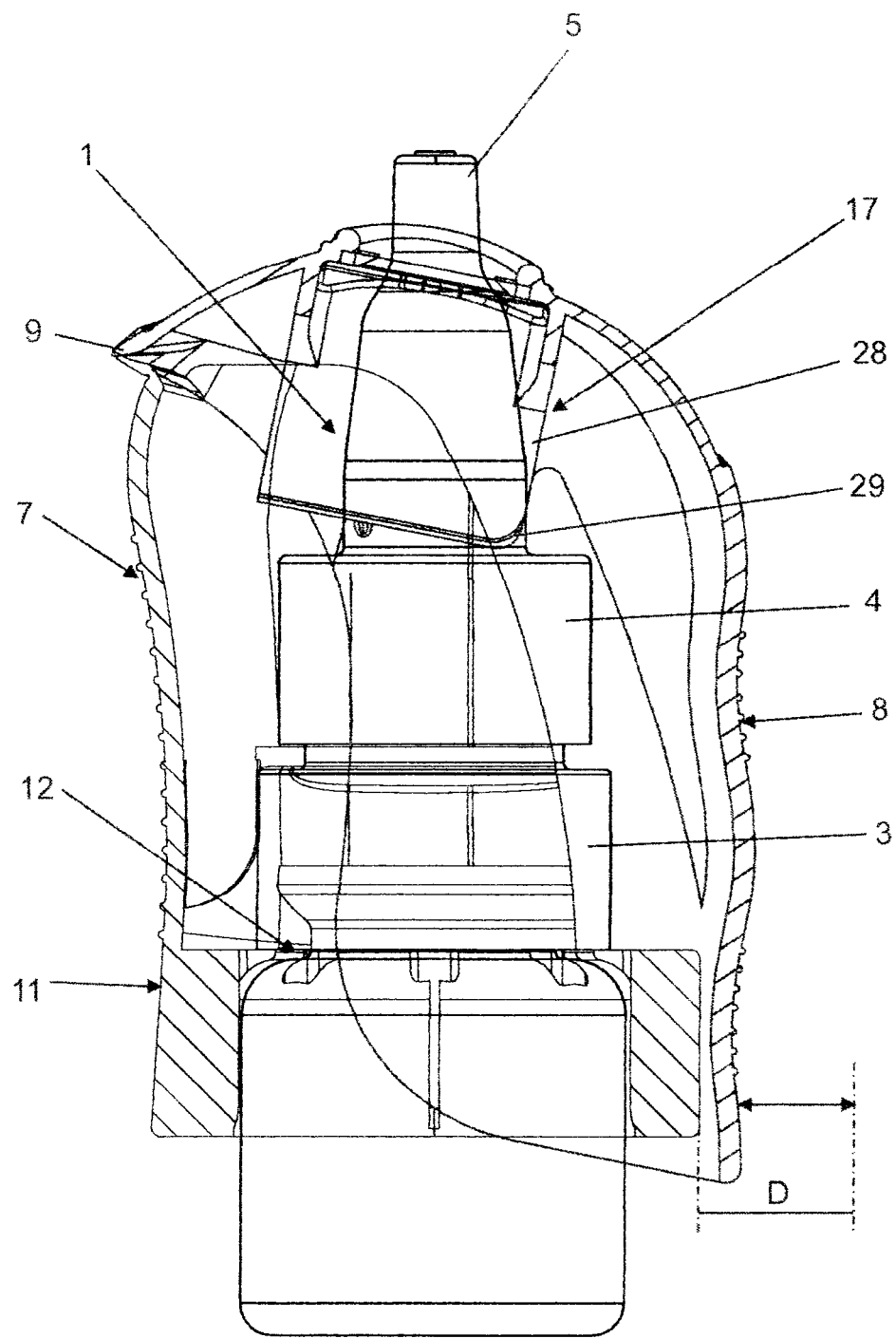

FIGS. 16 and 17 show, respectively, the combination in rest and driven status, wherein it is noted that the packaging (1) is simply fitted upwardly on the inside of the body (7) until the means (12) are positioned below the lid (3), at which moment there occurs the union and locking between the device and the primary packaging, and also the lower edge of the cam (17) or its walls (28) are positioned on the springed actuator (4). In this condition, the combination is ready to be used, it being suffice to remove the lid (21) and press the pressing cover (8) until its lower edge meets the base (11) and, with this, the cam (17), more precisely its walls (28) lean sufficiently for the corners (29) to press the springed actuator (4) downwards, consequently, a dosed quantity of medicine is dispensed through the nozzle (5). Refraining from pressing the cover (8), the entire combination automatically returns to the original position, maintaining itself in position for new drive.

What is claimed is:

1. A medicine dispensing device, comprising:
    a single injection molded part made of plastic material, said single injection molded part comprising a body and a cover pivotally interconnected by an articulation arranged on an upper edge of the body,
    said body having an annular base and a cylindrical encasement defining a longitudinal axis of the body and extending from an outer diameter of the base, said cylindrical encasement having an open side defined by side edges of the cylindrical encasement, said base having an inner diameter provided with fasteners for engaging between a flask and a lid of a primary medicinal packaging received in said cylindrical encasement for securing the primary medicinal packaging in the body,
    said cover having a cylindrical portion defining a longitudinal axis of the cover and an upper tapered dome-shaped portion with a circular through-opening, said cylindrical portion having an open side defined by side edges of the cylindrical portion, said cover having two cams arranged below the circular through-opening, said dome-shaped portion having a garret, said through-opening having a fastening collar,
    said cover being pivotal about the articulation so as to assume a first position in which the body is axially aligned with the cover and the side edges of the body slidably engage between the side edges of the cover and in which the cover engages with side retention means provided on the cylindrical encasement of the body, and in which a lower edge of the cover is spaced apart by a distance from the annular base, and a second position in which the cover contacts the annular base; and
    wherein in an initial injection molded state the longitudinal axis of the body and the longitudinal axis of the cover are disposed orthogonally to each other,
    wherein the two cams are arranged so as to rest in the first position of the cover on a springed actuator of the primary medicine packaging received in the body and to push the springed actuator down when the cover is moved to the second position,
    wherein the body and the cover are provided with anti-slip surfaces and together form a grip when the body and the cover are axially aligned, and
    wherein the annular base is formed by two concentric walls, an ovoid external wall and a circular internal wall, said two concentric walls being interconnected by radial walls and by an upper closure wall, said upper closure wall being integrated to the fasteners.

2. The medicine dispensing device of claim 1, further comprising another lid received on the garret, said another lid having an internal fast-engagement-clip for engagement with the fastening collar of the circular through-opening, said another lid covering an exposed part of a dispensing nozzle of the primary medicinal packaging device received in the body.

3. The medicine dispensing device of claim 1, wherein the fasteners are formed by a plurality of coplanar trapezoidal equidistant tabs extending from the upper closure wall and together defining an internal diameter slightly greater than an external diameter of the lid of the primary medicinal packaging and constructed to be resiliently displaced and to latchingly engage behind a lower edge of the primary medicinal packaging, upon insertion of the primary medicinal packaging in the body.

4. The medicine dispensing device of claim 1, wherein the two cams are formed by two vertical walls, extending on either side of the circular through-opening from an inner face of the dome-shaped portion, said two vertical walls having horizontally aligned lower edges which in the first position are in parallel relationship to the springed actuator of the primary medicine packaging.

5. The medicine dispensing device of claim 4, wherein the two vertical walls have rounded corners, forming support pressing points against the springed actuator of the primary medicine packaging.

6. The medicine dispensing device of claim 1, wherein, the side retention means are constructed in the form of opposite wedges disposed adjacent the side edges of the cylindrical encasement.

7. The medicine dispensing device of claim 1, wherein inner faces of the body and the cover have geometries that adjust against a profile of the primary medicinal packaging to stabilize a position of use of the medicine dispensing device.

8. The medicine dispensing device of claim 1, wherein the circular through-opening has a diameter sufficient to expose a dispensing nozzle and an original lid of the primary medicine packaging.

9. In combination:
    a medicine dispensing device, comprising a single injection molded part made of plastic material; and
    a primary medicinal packaging received in the medicine dispensing device and comprising a flask, a lid, a springed actuator and a dispensing nozzle,
    said single injection molded part comprising a body and a cover pivotally interconnected by an articulation arranged on an upper edge of the body,
    said body having an annular base and a cylindrical encasement defining a longitudinal axis of the body and extending from an outer diameter of the base, said cylindrical encasement having an open side defined by side edges of the cylindrical encasement, said base having an inner diameter provided with fasteners for engaging between the flask and the lid of the primary medicinal packaging received in said cylindrical encasement for securing the primary medicinal packaging in the body,
    said cover having a cylindrical portion defining a longitudinal axis of the cover and an upper tapered dome-shaped portion with a circular through-opening, said cylindrical portion having an open side defined by side edges of the cylindrical portion, said cover having two cams arranged below the circular through-opening, said dome-shaped portion having a garret, said through-opening having a fastening collar, said cover being pivotal about the articulation so as to assume a first position in which the body is axially aligned with the cover and the side edges of the body slidably engage between the side edges of the cover and in which the cover engages with side retention means provided on the cylindrical encasement of the body, and in which a lower edge of the cover is spaced apart by a distance from the annular base, and a second position in which the cover contacts the annular base; and wherein in an initial injection molded state the longitudinal axis of the body and the longitudinal axis of the cover are disposed orthogonally to each other, wherein the two cams are arranged so as to rest in the first position of the cover on the springed actuator of the primary medicine packaging received in the body and to push the springed actuator down when the cover is moved to the second position, and wherein the body and the cover are provided with anti-slip surfaces and together form a grip when the body and the cover are axially aligned, wherein the base is sized so that a lower part of the base exposes a part of a height of the flask of the primary medical packaging and wherein a bottom of the flask forms a standing support for the medicine dispensing device and the primary medicine packaging, and wherein the annular base is formed by two concentric walls, an ovoid external wall and a circular internal wall, said two concentric walls being interconnected by radial walls and by an upper closure wall, said upper closure wall being integrated to the fasteners.

* * * * *